United States Patent [19]

Manahan

[11] 4,360,014
[45] Nov. 23, 1982

[54] RESTRAINING GARMENT

[76] Inventor: Virginia M. Manahan, 4421 Browning Dr., Oxnard, Calif. 93030

[21] Appl. No.: 209,850

[22] Filed: Nov. 24, 1980

[51] Int. Cl.³ ............................................. A61F 13/00
[52] U.S. Cl. ..................................................... 128/134
[58] Field of Search ................................. 128/134, 133

[56] References Cited

U.S. PATENT DOCUMENTS

| | | | |
|---|---|---|---|
| 2,170,703 | 8/1939 | Waxman et al. | 128/134 |
| 3,566,864 | 3/1971 | Garrow | 128/134 |
| 3,641,997 | 2/1972 | Posey, Jr. | 128/134 |
| 3,779,540 | 12/1973 | Boudreau | 128/134 |
| 3,901,229 | 8/1975 | Hensel et al. | 128/134 |
| 4,026,282 | 5/1977 | Thomas | 128/134 |
| 4,050,737 | 9/1977 | Jordan | 128/134 |

Primary Examiner—Michael H. Thaler
Assistant Examiner—C. W. Shedd
Attorney, Agent, or Firm—Dennis L. Mangrum

[57] ABSTRACT

The present inventions relates to a garment for comfortably and securely confining a patient in a bed, chair or other supporting structure. The garment is a loose fitting gown disposed on the upper body that permits patient mobility on the supporting structure yet prevents escape by accident or otherwise. The garment is particularly suited for use on elderly hospital patients, invalids and the like, but may be used on other patients to be restrained. The garment can not be removed by the patient and has a waist and crotch restraining members which can be employed alternately and/or simultaneously for confining a patient to a bed, a chair, or other supporting structure.

7 Claims, 3 Drawing Figures

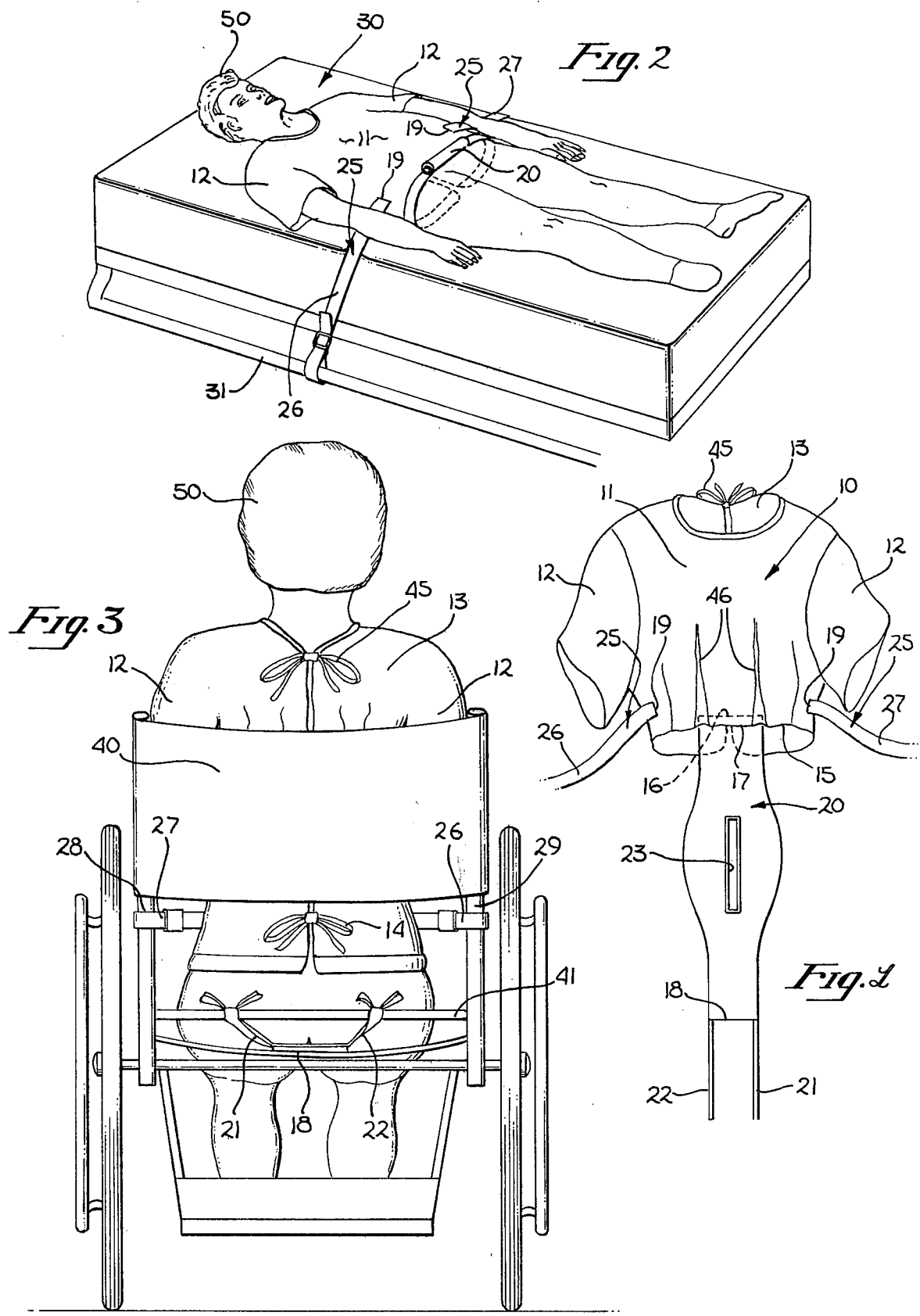

RESTRAINING GARMENT

BACKGROUND OF THE INVENTION

1. Field of the Invention

The present invention relates generally to restraining garments and specifically to restraining garments for the elderly, invalid or sick.

2. Prior Art

Confining or restraining devices and garments are well known in the art. Such devices are generally employed by medical personel where it is necessary to restrain or confine a persons movements on a specified supporting structure, in hospitals santariums, convalescent houses and the like. They are generally used on the elderly, invalid or sick for protective purposes. Many of these devices are unsatisfactory because or their expense, appearance, inconvenience, comfort, acceptance by a patient and/or ineffectiveness. The most pertinent of the prior art devices and their defficiencies are discussed hereinafter.

U.S. Pat. No. 4,132,230, issued to James T. Ladd, discloses a vest type garment with a chest and waist restraining member. The device is said to be constructed so that the patient can not remove it without help, excepy in emergency. Prevention of removability of the vest is accomplished by means of a crotch strap which is either buttoned or snapped into place, extending from the back to the front of the vest through the crotch. In use, this small strap is not effective in resisting removal of the garment. Additionally the vest configuration of the garment is such as to permit patients to slip their arms through the large armholes while undoing the crotch strap to remove the garment over the head. The small crotch strap also has problems associated with its thinness for irritating, and chaffing the patient when worn. The crotch strap also prevents a patient from using self help to eliminate waste products from the body.

U. S. Pat. No. 4,170,991 issued to Henry Y. Kella, is a bib type apparatus which is capable of holding a patient in a wheel chair. The device has straps which on one end secure the patients chest to the chair, while a pair of additional straps secure the buttocks to the lower portion of the chair. This device presents several problems not associated with the present invention. It is a separate item which must be maintained in stock and carried around or stored between uses. It is not part of the wearing apparel of the patient and must be held ready for use. The device is not capable of securing a person to a bed but is only used for securing a sitting person to a chair. The device causes problems in breathing, and prevents mobility. The chest strap should not be used on patients who have any type of breathing problem.

U.S. Pat. No. 4,026,282, issued to Lois Thomas, is a dressing gown which has two belts, one disposed on each side of the gown near the waist area. The straps are disposed so that they can cross one another and be seecured to a bed or other supporting structure. The problem with this gown is that the straps are sewn securely to the body, and to securely fasten a person to a supporting structure the body must itself be securely fastened. A patient confined to bed for long durations must have loosely fitting clothes or bed sores will easily develop. Tight garments create bed sores much faster than loose garments. This snuggly fitting type restraint also prevents patient examination while being worn.

Additionally it must be noted that neither patients nor visitors nor family desire to see their relatives "strapped, like a prisoner", into a bed. This device usually appears as such a garment and is disliked by all. In order to perform properly the belts must be securely fastened to the bed such that the patient is restrained from moving to the point that any mobility at all is severly restricted. It becomes difficult for a patient to change positions and impossible for the patient to move from a prone to a sitting position. All patients require mobility on the supporting structure but need restraint to prevent a fall.

U.S. Pat. No. 4,208,170, issued to Donald C. Spann, is a support strap for restraining a patient either in a chair or in a bed. The device is simple in that it is simply a strap which goes around the chest of the user and around the chair or other supporting structure. As previously noted these type of device impairs and makes breathing difficult. It is an additional item which must be stocked or stored separate from gowns by the medical care unit for use when necessary. Many elderly patients have difficulty breathing. Any impairment across the chest which limits the breathing ability is detrimental to the patient. This and other devices having chest straps are particularly not useful for elderly people.

None of the above prior art provide a gown or garment which can be worn by any hospital patient which has the capabilities of securely fastening a patient to a bed, chair, or other supporting surface while permitting the patient to have mobility to move, roll, sit, or lie. Additionally, no other prior art device has a garment which has the capability of being loosened independently of the restraining straps yet prevents independent patient removal. No other prior art device has a diaper type strap which is designed to prevent sores while permitting a patient to eliminate waste from his body, without help.

The present invention provides a garment which overcomes all the problems of the prior art and provides a garment which is comfortable to wear, which restrains a person while resting on a structure, permitting mobility, yet preventing fall or escape. The garment can be used as a restraining device either on a bed, chair, wheelchair, or other supporting structures without modification, or without additional attachments.

SUMMARY OF THE INVENTION

An upper body garment for comfortably and securely confining a person to a bed, chair or other supporting surface is disclosed. The garment is comprised of; sleeves to prevent patient removal; a belt disposed through the body near the waist to secure the patient to the supporting member; and a crotchstrap to provide additional restraint for a person sitting in a chair or the like. The garment permits examination, and normal bed movement but restrains the user from falling or escaping. It is sanitary and it does not appear to the patient or visitors as a "straight jacket".

It is an object of the invention to provide a restraining confining garment which can not be removed by the patient alone, which permits normal bed movement, such as changes of position (change of position from sitting to lying) without assistance of an aide, while preventing the patient from falling or escaping from the supporting surface.

It is an object of the present invention to provide an inexpensive, safe garment capable of being mass manufactured and stocked by medical personnel for the restraining of elderly people, invalids, and/or patients under medical care.

It is still another object of the present invention to provide a device which does not appear as a "straight jacket" either to the patients or to visitors.

It is another object of the present invention to provide a sanitary, comfortable device which can be used as a normal medical patient blouse, permitting examination while acting as a restraint.

BRIEF DESCRIPTION OF THE DRAWINGS

FIG. 1, is a front view of the garment of the present invention;

FIG. 2, is a perspective view of a patient wearing the garment of the present invention and being secured to the bed by said garment;

FIG. 3, is a back view of a patient sitting in a wheel chair wearing the garment of the present invention and being restrained in place hereby.

DETAILED DESCRIPTION OF THE PREFERRED EMBODIMENT

The present invention is a garment covering the upper portion of a persons body and is used as a hospital gown for securely and comfortably confining a person to a bed, chair or other supporting surface. The garment is best illustrated and referred to in FIG. 1. It should be noted that the garment illustrated in FIG. 1 is the preferred embodiment of the present invenion and that various changes may be made in the design and concept without changing the invention. However, the invention claimed herein will be described in reference to the preferred embodiment.

Referring first to FIG. 1, the various general components of the preferred embodiment will be described. The garment 10 is formed of a body portion 11 which serves to cover the upper torso of a person and could generally be described as a blouse. The blouse has sleeves 12 which must be of some substance and should extend at least to near the elbow. The garment 10 opens from the back 13. The back is fastened together by a series of ties 14. In the preferred form the ties are strings; but snaps buttons or other means of securing the garment could be employed. Upper tie 45 is used to secure to very uppermost portions of the neck of the blouse.

The blouse is designed to extend to just below the waist of the wearer and should be loose fitting for the person on which it is employed. A belt 25 is disposed through preformed slots 19 in the garment. The slots 19 are disposed near the waist and on each side of the blouse. End 26 of belt 25 extends from one side of the garment while end 27 extends from the other side of the garment. Thus the belt 25 extends across the waist of the person beneath the garment so as not to be visible and protrudes from the slots 19 to permit the ends thereof to be fastened to the supporting structure.

A crotchstrap 20 is formed as a part of the blouse and is disposed at the front waist seam 17. The strap 20 is an elongated member which is capable of being disposed through the crotch of the patient. An elongated slot 23 is disposed in midportion the strap 20 as illustrated in FIG. 1. Ties 21 and 22 are disposed on end 18 which are tied to a supporting member, i.e., a wheel chair.

The garment of the present invention and the parts thereof can be formed in the preferred form of the invention of a cotton fabric or cotton-polyester material. Optionally a canvas weave and other suitable material could be utilized.

Having now described the physical form and parts of the present invention their use and application will be described. The garment 10 is secured about the patient by ties 14. The opening of the garment is disposed in the back 13 of the garment 10, to prevent the patient from removing it without assistance. Upper tie 45 is used to form a narrow opening for the neck so as to prevent a patient from slipping the garment over his or her head. The sleeves 12 are formed of such a length so as to prevent a patient from slipping his elbow into the body portion of the garment 10 and thereafter removing it over his head. Prior art vests and the like can be removed by the wearer by simply slipping the arms out and pulling it over the head. Sleeves as illustrated in preferred form of the invention prevent such removal.

Referring now to FIG. 2 a patient 50 is shown confined to a bed 30. The belt 25 is shown protruding through either side of the waist of the garment 10 with end 26 secured to bed rail 31 and end 27 secured to an opposite bed rail. Various fastening members can be used to secure the ends of the belt 25 to the bed, post, or rail or other parts. In the preferred form velcro strips are used.

The belt 25 is slideably disposed within garment 10 and through slots 19. This permits the patient to freely adjust the garment to desired positions, to and have it loosely fitting thereby reducing substantially soreness by chafing, even though the restraining belt 25 is securely fastened to prevent the patient from falling or escaping from the bed 30. This placement of belt 25 so as to be in the position about the waist of the patient permits the patient to either sit or lie without adjustment. The location of the belt is such that it does not interfere with breathing of patient, whereas, placement of the belt at or about the chest restricts the breathing and is dangerous to many confined patients. Placement of the belt about the waist of the patient also permits the patient to shift about within the bed without falling therefrom. Pleats 46 are disposed within the front of the garment to provide ample space for adjustment and loose fitting of both male and female patients. In this view, FIG. 1, and in this form of the present invention, does not appear to either the patient or the visitors that he is being confined as if in a "straight jacket". In fact the patient cannot even see the belt except when it protrudes over the sides of the bed. In normal use the bed covering usually covers the exposed ends 26 and 27 so that the visitors cannot even see the belt.

It should be noted that the crotchstrap 20 in the preferred form, is not used when the patient is being confined to a bed, supporting structure, or the like. Instead the strap 20 is rolled up and secured by velcro strips or other fastening means at the waist of the patient. In cases where the patient is a real threat to escape the strap can be fastened in place by securing ends 21 and 22 to the back 13 of the blouse 10 making it extremely difficult to remove without aid.

Referring now to FIG. 3, the device is shown in use on the patient 50 while sitting in the wheel chair 40. In this use belt 25 is disposed as previously described and secured to opposing handrails, 28 and 29, by ends 26 and 27 respectively. Belt 25 is disposed at about waist level of the patient so as to prevent the patient from falling from the wheel chair 40. Strap 20 is utilized in this application of the invention and disposed through the crotch of the patient such that the tie straps 21 and 22 can be secured to bar 41 of the wheel chair. The purpose of strap 20 is to restrain the lower body of the patient from slipping out of the wheel chair 40. It should be noted that the strap 20 has a widened area in the center so as to reduce chafing and soreness. Appature 23 is so disposed as to permit a patient to eliminate bodily fluids while sitting in the chair. The patient may accomplish this without assistance and provides a great benefit to the elderly and invalid people restrained to wheel chairs.

The preferred form of the present embodiment of the invention has been described in physical detail, in use and application. It provides a single unit which can be used by all hospitals and the like for use by the elderly, invalids, and other patients which need to be restrained either in the chair or bed. It eliminates the need to store both blouses and additional securing items separate and can save greatly in hospital and medical expenses related to such items. The device is easily used, easily maintained and can be used as a hospital gown for patients not needing restraints. The preferred embodiment of the present invention has been described in detail herein, however it will be understood by those skilled in the art that various changes in form and detail may be made therein without departing from the spirit and scope of the invention.

I claim:

1. A garment for comfortably confining and securing a person to bed, chair or other supporting structure while permitting relatively free movement upon said supporting structure, said garment comprising:
    (a) a body member fitting about the torso of said person and having apertures therein;
    (b) sleeve members, through which the arms of said person may be disposed;
    (c) fastening means for securing said body member about the torso of said person, said fastening means for snugly forming the neck opening;
    (d) a single belt means disposed through said apertures in said body member, positioned such that said single belt means is disposed at the waist of said person, said belt means capable of being coupled to said supporting structure on either side of said person for confining said person to said supporting structure while permitting relative freedom of movement upon said supporting structure, said belt means being separate and not coupled to said body member permitting independent adjustment of said body member;
    (e) a strap means coupled to the front lower portion of said body member, said strap means capable of being disposed through the crotch of said person and being secured behind the buttock of said person to a said supporting structure or to a lower portion at the rear of said body member.

2. The garment of claim 1, wherein said strap means is of sufficient width to prevent chafing and cutting.

3. The garment of claim 1, wherein said strap means has an elongated aperture disposed therein to permit a person to excrete body waste without having to remove said garment.

4. The garment of claim 1, wherein said supporting structure is a chair, and said strap means restrains the lower body of said person.

5. The garment of claim 1, wherein said strap means is capable of being rolled up and secured in place to said body member when said strap means is not being used.

6. A garment for comfortably confining and securing a person to a bed, chair or other supporting structure while permitting relatively free movement upon said supporting structure, said garment comprising;
    (a) a body member fitting about the torso of said person and having an opening at the back thereof and apertures therein;
    (b) fastening means disposed at said opening to secure said body member about the torso of said person; said fastening means for snugly forming at least a neck closure;
    (c) sleeve members attached to said body member through which the arms of said person are disposed, of sufficient length to prevent said person from withdrawing his arms therefrom and into said body member when said fastening means is fastened, said sleeve members preventing said person from removing said garment;
    (d) a single belt means disposed through at least two apertures in the lower portion of said body member, said apertures disposed such that the ends of said belt means protrude from opposite sides of said garment, said ends being securable to said supporting structure; said belt means, being separate and not coupled to said body member, have a portion thereof disposed beneath said garment and about the waist of said person for confining said person to said supporting structure while permitting adjustment of the garment and relative freedom of movement upon said supporting structure;
    (e) a strap means coupled to a front lower portion of said body member and being capable of alternate ways of securement such that when said person is reclining on a said supporting structure, said strap means is disposed through the crotch of said person and secured to a lower rear portion of said body member thereby preventing removal of said body member by said person; when said supporting structure is a chair or the like, said strap means is disposed through the crotch of said person and secured behind said person's buttock to said supporting structure and thereby restraining the lower body of said person thereon; said strap means being of sufficient width to prevent chafing and cutting and having an elongated aperture disposed therein to permit a person to excrete body waste therethrough.

7. The garment of claim 6 wherein pleats are disposed in said garment such that said garment is loose fitting, permits examination and prevents chafing, cutting and binding of said person.

* * * * *